(12) United States Patent
Neumann

(10) Patent No.: US 11,875,889 B2
(45) Date of Patent: Jan. 16, 2024

(54) METHODS AND SYSTEMS OF ALIMENTARY PROVISIONING

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC.

(*) Notice: Subject to any disclaimer, the term of this patent is extended or adjusted under 35 U.S.C. 154(b) by 796 days.

(21) Appl. No.: 16/888,303

(22) Filed: May 29, 2020

(65) Prior Publication Data

US 2021/0375428 A1 Dec. 2, 2021

(51) Int. Cl.
*G16H 20/60* (2018.01)
*G16H 40/67* (2018.01)
*G06N 20/00* (2019.01)

(52) U.S. Cl.
CPC ............. *G16H 20/60* (2018.01); *G06N 20/00* (2019.01); *G16H 40/67* (2018.01)

(58) Field of Classification Search
CPC ........ G16H 20/60; G16H 50/70; G16H 50/20; G16H 10/60
See application file for complete search history.

(56) References Cited

U.S. PATENT DOCUMENTS 7,894,849 B2 2/2011 Kass et al.
8,409,104 B2 4/2013 Cobain
(Continued)

FOREIGN PATENT DOCUMENTS

WO 2018020239 2/2018
WO WO-2021150926 A1 * 7/2021 ............ G06Q 20/12

OTHER PUBLICATIONS

Van Pinxteren, Youri, Gijs Geleijnse, and Paul Kamsteeg. "Deriving a recipe similarity measure for recommending healthful meals." Proceedings of the 16th international conference on Intelligent user interfaces. 2011. (Year: 2011).*

(Continued)

*Primary Examiner* — Jason B Dunham
*Assistant Examiner* — Constantine Siozopoulos
(74) *Attorney, Agent, or Firm* — Caldwell Intellectual Property Law

(57) ABSTRACT

A system for alimentary provisioning includes a computing device configured to provide an alimentary instruction set including a plurality of target nutrient quantities, receive, from each alimentary provider device of a plurality of alimentary provider devices, a plurality of provider ingredients, generate a plurality of ingredient combinations, wherein each ingredient combination is a combination of two or more provider ingredients of the plurality of provider ingredients, and select a plurality of beneficial ingredient combinations from the plurality of ingredient combinations, wherein selecting each ingredient combination of the plurality of ingredient combinations includes determining a nutrient listing corresponding to each ingredient combination of the plurality of ingredient combinations, creating a distance metric from the nutrient listing to the alimentary instruction set, and selecting at least an ingredient listing that minimizes the distance metric, and selecting the plurality of beneficial ingredient combinations to minimize the distance metric.

18 Claims, 4 Drawing Sheets

(56) References Cited

U.S. PATENT DOCUMENTS

| | | |
|---|---|---|
| 8,532,938 B2 | 9/2013 | Jung et al. |
| 8,737,971 B2 | 5/2014 | Van Rooyen |
| 8,762,167 B2 | 6/2014 | Blander et al. |
| 8,822,225 B2 | 9/2014 | Gotch et al. |
| 9,132,219 B2 | 9/2015 | Akonur et al. |
| 9,183,757 B2 | 11/2015 | Yamada et al. |
| 9,589,480 B2 | 3/2017 | Ellis |
| 9,758,839 B2 | 9/2017 | Apte et al. |
| 9,838,508 B2 | 12/2017 | Salem |
| 10,102,345 B2 | 10/2018 | Yanev et al. |
| 10,127,361 B2 | 11/2018 | Hyde et al. |
| 10,133,849 B2 | 11/2018 | Yanev et al. |
| 2008/0177149 A1 | 7/2008 | Weinert et al. |
| 2008/0195594 A1 | 8/2008 | Gerjets et al. |
| 2008/0306763 A1 | 12/2008 | James |
| 2010/0098809 A1 | 4/2010 | Bender et al. |
| 2013/0079612 A1 | 3/2013 | Hunt et al. |
| 2013/0138447 A1 | 5/2013 | Nova et al. |
| 2015/0012295 A1 | 1/2015 | Mahoney |
| 2016/0042152 A1 | 2/2016 | Oran |
| 2017/0216518 A1 | 8/2017 | Davis et al. |
| 2018/0032698 A1 | 2/2018 | Lau et al. |
| 2019/0228855 A1* | 7/2019 | Leifer .................. G06N 20/10 |
| 2019/0290172 A1* | 9/2019 | Hadad .................. G06N 20/00 |
| 2021/0104322 A1* | 4/2021 | Narayan ............... G06N 3/045 |

OTHER PUBLICATIONS

Westerman, et al.; Longitudinal analysis of biomarker data from a personalized nutrition platform in healthy subjects; Scientific Reports; Oct. 2, 2018; https://www.nature.com/articles/s41598-018-33008-7.pdf.

Inside Tracker; Who we are; file:///C:/Users/LindseyPowell/Downloads/InsideTracker's%20expert%20team_%20scientists...pdf.

Bald, Eric; The A.I. Diet; https://www.weizmann-usa.org/news-media/in-the-news/the-ai-diet.

Ramachandran, Swaroopini; Mar. 15, 2019; The algorithm to a perfect diet-AI has answers; http://peasonmoss.com/2019/03/15/the-algorithm-to-a-perfect-diet-ai-has-answers/.

VK, Anirudh; 5 AI-Powered fitness startups in India who are using data science to promote healthy lifestyle; https://www.analyticsindiamag.com/5-ai-powered-fitness-startups-in-india-who-are-using-data-science-to-promote-healthy-lifestyle/.

* cited by examiner

METHODS AND SYSTEMS OF ALIMENTARY PROVISIONING

FIELD OF THE INVENTION

The present invention generally relates to the field of artificial intelligence. In particular, the present invention is directed to methods and systems of alimentary provisioning.

BACKGROUND

Existing solutions for selection of a best fit for alimentary provisioning based upon physiological dictates have generally avoided dealing with the multiplicity of possible solutions by limiting sources or possible selections. This can lead to frustration and under-utilization, which can negate many of the benefits of such solutions.

SUMMARY OF THE DISCLOSURE

In an aspect, a system for alimentary provisioning includes a computing device configured to provide an alimentary instruction set including a plurality of target nutrient quantities, receive, from each alimentary provider device of a plurality of alimentary provider devices, a plurality of provider ingredients, generate a plurality of ingredient combinations, wherein each ingredient combination is a combination of two or more provider ingredients of the plurality of provider ingredients, and select a plurality of beneficial ingredient combinations from the plurality of ingredient combinations, wherein selecting each ingredient combination of the plurality of ingredient combinations includes determining a nutrient listing corresponding to each ingredient combination of the plurality of ingredient combinations, creating a distance metric from the nutrient listing to the alimentary instruction set, and selecting at least an ingredient listing that minimizes the distance metric, and selecting the plurality of beneficial ingredient combinations to minimize the distance metric.

In another aspect, a method of alimentary provisioning, the method comprising includes providing an alimentary instruction set including a plurality of target nutrient quantities, receiving, from each alimentary provider device of a plurality of alimentary provider devices, a plurality of provider ingredients, generate a plurality of ingredient combinations, wherein each ingredient combination is a combination of two or more provider ingredients of the plurality of provider ingredients, and selecting a plurality of beneficial ingredient combinations from the plurality of ingredient combinations, wherein selecting each ingredient combination of the plurality of ingredient combinations further includes determining a nutrient listing corresponding to each ingredient combination of the plurality of ingredient combinations, creating a distance metric from the nutrient listing to the alimentary instruction set, and selecting at least an ingredient listing that minimizes the distance metric, and selecting the plurality of beneficial ingredient combinations to minimize the distance metric.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments described herein perform alimentary provisioning, from a plurality of potential alimentary providers, starting with an alimentary instruction set detailing nutritional requirements. Available ingredients may be determined, per provider or generally, and compiled into ingredient combinations. The latter may be classified to categories close to the alimentary instruction set according to a distance metric to identify beneficial ingredient combinations. Selection of provider ingredient combinations may then be performed by minimizing loss functions to select one or more best-fit, recommended combinations. User inputs may be used to make a final selection, or to set criterial for recommendation.

Figure 1:
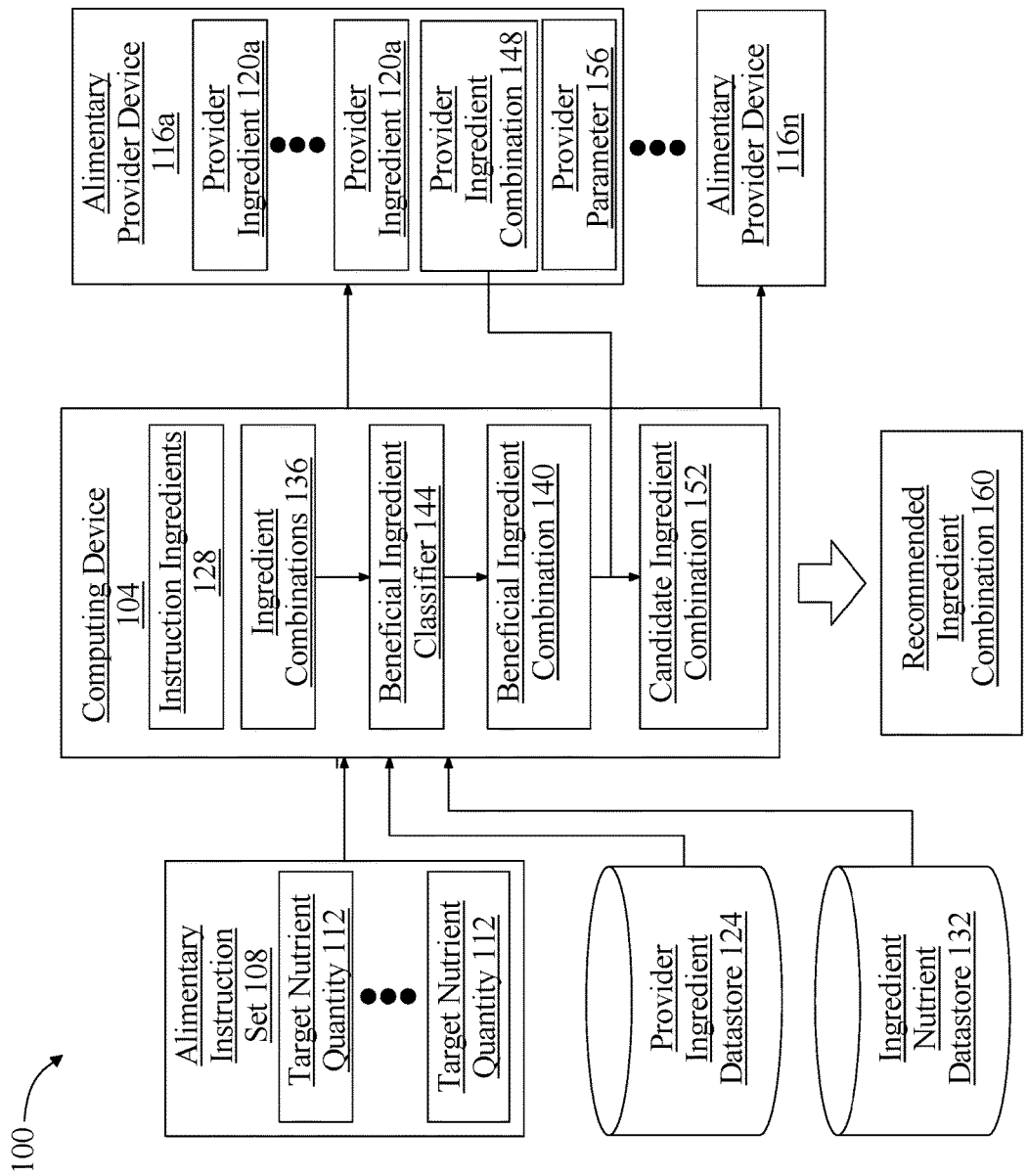
FIG. 1 is a block diagram of an exemplary embodiment of a system for alimentary provisioning.

Referring now to FIG. 1, an exemplary embodiment of a system 100 for alimentary provisioning is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication.

In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to provide an alimentary instruction set 108 including a plurality of target nutrient quantities 112. As used in this disclosure, an "alimentary instruction set" is a list or other collection of nutritional recommendations for a user, including recommendations of foods, nutrients, ingredients, and/or quantities thereof, that a user should consume for improved and/or optimal health. As used in this disclosure, a "target nutrition quantity" is a quantity of a given nutrient that alimentary instruction set 108 recommends user to consume. Quantities may include numbers representing a maximal amount to be consumed, a minimal amount to be consumed, and/or a precise amount that is determined to be ideal. Quantity may be zero for a nutrient that a user should not receive, and/or for a nutrient having no positive health benefit; for instance, a user who is diabetic may be recommended a quantity of zero for glucose, sucrose, or the like.

In a non-limiting embodiment, and further referring to FIG. 1, computing device 104 may provide alimentary instruction set 108 by receiving training data, recording at least a biological extraction from a user, training a machine-learning process using the training data, and, generating the at least an alimentary instruction set 108 as a function of biological extraction and using the machine-learning process. "training data," as used herein, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and continuing to refer to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatically may enable the same training data to be made applicable for two or more distinct machine-learning algorithms as described in further detail below. Training data used by computing device 104 and/or another device may correlate any input data as described in this disclosure to any output data as described in this disclosure.

Still referring to FIG. 1, A "machine learning process," as used in this disclosure, is a process that automatedly uses a body of data known as "training data" and/or a "training set" to generate an algorithm that will be performed by a computing device 104/module to produce outputs given data provided as inputs; this is in contrast to a non-machine learning software program where the commands to be executed are determined in advance by a user and written in a programming language. Generation of alimentary instruction set 108 using machine learning may be implemented, without limitation, as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Alternatively or additionally, alimentary instruction set 108 may be received from user, from a medical professional, a nutritionist, and/or from one or more remote devices, including devices operated by user, by a medical professional, or the like.

Still referring to FIG. 1, computing device 104 is configured to receive, from each alimentary provider device of a plurality of alimentary provider devices 116, a plurality of provider ingredients 120. An alimentary provider device may include any device suitable for use as computing device 104, as described above, which is operated by an alimentary provider. An "alimentary provider," as used in this disclosure, is a person or entity that prepares alimentary products such as meals, food items, and/or drinks, including without limitation a restaurant, a food delivery service, or the like. Provider ingredients may include any ingredient or ingredients, where "ingredients" are defined as any ingredient in any alimentary product. In an embodiment, each alimentary provider device may indicate a time period, such as a date range, during which each ingredient is available, a geographic region within which each ingredient is available, or the like; alternatively or additionally, each alimentary provider device may solely indicated current availability of each ingredient and/or report only ingredients that are available from an alimentary provider associated with the alimentary provider device at the time that transmission occurs. Computing device 104 may store received provider ingredients in a provider ingredient datastore. Provider ingredient datastore may include any data structure for ordered storage and retrieval of data, which may be implemented as a hardware or software module. A provider ingredient datastore may be implemented, without limitation, as a relational database, a key-value retrieval datastore such as a NOSQL database, or any other format or structure for use as a datastore that a person skilled in the art would recognize as suitable upon review of the entirety of this disclosure. A provider ingredient datastore may include a plurality of data entries and/or records as described above. Data entries in a provider ingredient datastore may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a provider ingredient datastore may reflect categories, cohorts, and/or populations of data consistently with this disclosure. Provider ingredient datastore may be located in memory of computing device 104 and/or on another device in and/or in communication with system 100.

Figure 2:
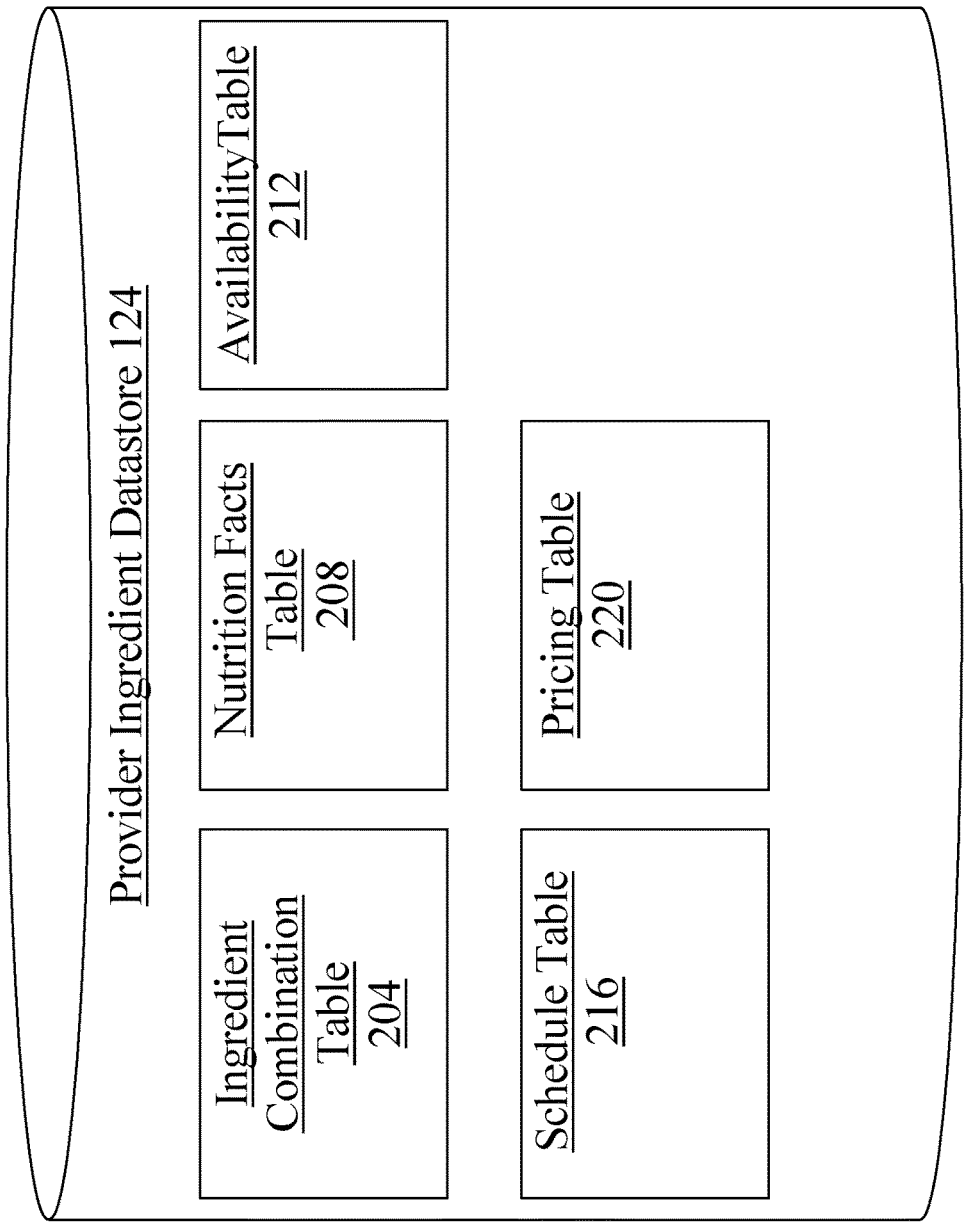
FIG. 2 is a block diagram of an exemplary embodiment of a provider ingredient datastore.

Referring now to FIG. 2, provider ingredient data store 124 may include an ingredient combination table 204, which may list ingredients used in each ingredient combination. Provider ingredient data store 124 may include nutrition facts table 208, which may list nutrition quantities present in one or more ingredients and/or ingredient combinations; this may be used for comparison and distance metric and described in further detail herein. Provider ingredient data store 124 may include an availability 212, which may indicate ingredients and/or ingredient combinations that are currently available. Provider ingredient data store 124 may include a schedule table 216, which may indicate when ingredients and/or ingredient combinations are and/or have been available, for instance on a seasonal basis and/or according to production by one or more suppliers. Provider ingredient data store 124 may include a pricing table 220, which may describe prices for ingredients and/or ingredient combinations.

Referring again to FIG. 1, computing device 104 may group provider ingredients within provider ingredient data store according to a geographical region in which the provider ingredients are available, a time period during which the provider ingredients are available, and/or any other category that may be defined by data associated with any provider ingredient as described in this disclosure. Provider ingredients may be grouped in provider ingredient datastore according to identifiers of alimentary provider devices, and/or associated alimentary providers, that transmitted provider ingredients; in other words, computing device 104 and/or other devices in and/or communicating with system 100 may be able to query provider ingredient datastore using an identifier of an alimentary provider and receive in return a list of ingredients currently available to that provider and/or that will be available to that alimentary provider within a given time period and/or at a particular location.

In an embodiment, and still referring to FIG. 1, receiving plurality of provider ingredients may include transmitting, to each alimentary provider device, a plurality of instruction ingredients 128. "Instruction ingredients," as used in this disclosure, are ingredients associated with alimentary instruction set 108. Computing device 104 may identify one or more instruction ingredients using an ingredient nutrient datastore 132, which may be implemented using any datastore suitable for use as provider ingredient datastore. Ingredient nutrient datastore may associate each ingredient of a plurality of ingredients with one or more nutrients contained in the ingredient, as well as amounts of each such nutrient available per a given quantity of the ingredient, such that querying ingredient nutrient datastore using one or more nutrients provided in alimentary instruction set 108 may return a list of ingredients containing the one or more nutrients; query may be implemented as a compound query, that returns ingredients containing selected combinations of nutrients as well as a single query returning any ingredients containing a single nutrient, or the like. Such ingredients may be transmitted to each alimentary provider device, permitting alimentary provider device and/or a user thereof to indicate each ingredient, of the instruction set ingredients, that alimentary provider is able to use and/or procure. In an embodiment, this may enable alimentary providers to indicate not only ingredients that they currently have in stock, but also ingredients they are able to acquire in a timely manner. Computing device 104 may receive from each alimentary provider device, a plurality of matching ingredients. In an embodiment, alimentary provider devices may provide both a list of ingredients currently offered, as described above, and a set of selections of instruction ingredients as described above. Computing device 104 may identify plurality of instruction ingredients as a function of the target nutrient quantities using ingredient nutrient datastore.

Still referring to FIG. 1, computing device 104 may be configured to generate a plurality of ingredient combinations 136, wherein each ingredient combination is a combination of two or more provider ingredients of the plurality of provider ingredients. In an embodiment, this may be accomplished by generating possible combinations of provider ingredients and/or all possible combinations of provider ingredients available from a given provider; alternatively or additionally combinations may be limited to previously reported combinations, such as combinations indicated and/or submitted by one or more alimentary provider devices, and/or listed by one or more expert users. Combinations may be limited to provider ingredients each of which includes at least one nutrient of plurality of target nutrient quantities.

Continuing to refer to FIG. 1, computing device 104 may be configured to select a plurality of beneficial ingredient combinations 140 from the plurality of ingredient combinations. A "beneficial ingredient combination," as used in this disclosure, is a combination of ingredients that tends to improve health of a user, as determined by a degree to which the beneficial ingredient combination provides nutrients matching target nutrient quantities. In an embodiment, matching target nutrient quantities may be accomplished by matching ingredient combinations to all of target nutrients. Alternatively, computing device 104 may match ingredient combinations' nutrients to a subset of target nutrients. For example, and without limitation, where user has already consumed some of target nutrients and/or some portion of one or more target nutrients' quantities as set forth in alimentary instruction set 108, computing device 104 may remove such consumed nutrients and compare only to target nutrients and/or quantities thereof that have not yet been consumed. Computing device 104 may select each ingredient combination of plurality of ingredient combinations by determining a nutrient listing corresponding to each ingredient combination of the plurality of ingredient combinations, creating a distance metric from the nutrient listing to the alimentary instruction set 108, and selecting at least an ingredient listing that minimizes the distance metric, and selecting the plurality of beneficial ingredient combinations to minimize the distance metric. A "distance metric," as used in this disclosure, is a quantitative value indicating a degree of similarity of a set of data values to another set of data values. For instance, and without limitation, combinations of nutrient quantities associated with each ingredient combination, and target nutrient quantities of alimentary instruction set 108, may be represented a vector. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance metric may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting illustration, target nutrients from alimentary instruction set 108, and/or one or more subsets thereof, may be represented using a vector or other data structure, and nutrients provided by each ingredient combination of plurality of ingredient combinations may be represented by a like data structure, such as another vector; a distance metric comparing the two data structures may then be calculated and compared to distance metrics calculations to find a minimal distance metric calculation and/or a set of minimal distance metric calculations. A set of minimal distance metric calculations may be a set of distance metric calculations less than a preconfigured threshold distance from data structure representing target nutrients. Preconfigured threshold may be set by one or more expert users and/or determined statistically, for instance by finding a top quartile and/or number of percentiles of proximity in a series of distance metric determinations over time for user, at one time for a plurality of users, and/or over time for a plurality of users. Plurality of users may include a plurality of users selected by a user classifier, which may classify user to a plurality of users having similar physiological data and/or user data; implementation of a user classifier may be performed, without limitation, as described in U.S. Nonprovisional application Ser. No. 16/865,740, filed on May 4, 2020 and entitled "METHODS AND SYSTEMS FOR SYSTEM FOR NUTRITIONAL RECOMMENDATION USING ARTIFICIAL INTELLIGENCE ANALYSIS OF IMMUNE IMPACTS," the entirety of which is incorporated herein by reference. In an embodiment, a distance metric may include a measurement of an optimization of one or more factors that include distance, price, quality and/or availability.

In an embodiment, and further referring to FIG. 1, neutral ingredients and/or neutral nutrients may be excluded from data structures used in distance metric calculations and/or classification as described in further detail below. A "neutral ingredient" as used in this disclosure is an ingredient that has not been determined to have a measurable negative or positive effect on health, such as some seasonings, spices, or the like. In an embodiment, system 100 may not map neutral ingredients to nutrients; for instance, ingredient nutrient datastore may not list nutrients for a neutral ingredient. Alternatively or additionally a nutrient having no measurable positive or negative health effect, referred to for purposes of this disclosure as a "neutral nutrient," may be listed in ingredient nutrient datastore, but excluded from distance metric and/or classification calculations. As a non-limiting example, two foods having ingredients differing only by neutral ingredients and/or neutral nutrients may thus be treated by system 100 as equivalent.

Still referring to FIG. 1, beneficial ingredient combinations may be selected using a beneficial ingredient classifier 144. A "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements. KNN algorithm may operate according to any suitable distance metric, including without limitation vector similarity as described above.

Continuing to refer to FIG. 1, beneficial ingredient classifier may be trained by computing device 104 and/or other devices in system using training data associating nutrient quantities and/or sets of nutrient quantities to ingredient combinations recorded as having been used, for instance, in meals and/or servings in the past. Beneficial ingredient classifier may generate a plurality of categories of combinations of nutrients, each including at least one target nutrient quantity matching alimentary instruction set 108, and may classify ingredient combinations to such categories; in an embodiment, ingredient combinations classified to categories closer to alimentary instruction set 108 according to distance metric may be labeled as beneficial ingredient combinations.

Still referring to FIG. 1, computing device 104 may select a plurality of candidate ingredient combinations 152 from a plurality of provider ingredient combinations 148 offered by alimentary providers. A "provider ingredient combination," is defined for the purposes of this disclosure as a combination of ingredients that an alimentary provider and/or alimentary provider device indicates may be provided, for instance and without limitation in the form of a meal. "Candidate ingredient combinations," for the purposes of this disclosure, are provider ingredient combinations selected as beneficial to user's health, according to alimentary instruction set 108. Determination that a provider ingredient combination is beneficial may be accomplished by selection of a provider ingredient combination to minimize a distance from a beneficial ingredient combination as measured using a distance metric. For instance, computing device 104 may select plurality of candidate ingredient combinations by receiving, from each provider device, a plurality of provider ingredient combinations and selecting a plurality of candidate ingredient combinations matching a beneficial ingredient combination of the plurality of beneficial ingredient combinations; matching may be determined using beneficial ingredient classifier as described above. Alternatively or additionally, selecting the at least a provider ingredient combination may include generating a distance metric from each provider ingredient combination of the plurality of provider ingredient combinations to beneficial ingredient combinations of the plurality of beneficial ingredient combinations, and selecting the at least a provider ingredient combination that minimizes the distance metric.

The above-described processes may be combined; for instance, each provider ingredient combination may be classified to a beneficial ingredient combination using beneficial ingredient classifier, and a distance metric from provider ingredient combination to beneficial combination may be calculated and compared to a preconfigured threshold, where a distance falling below a threshold quantity may cause provider ingredient combination to be selected as a candidate ingredient selection. In an embodiment, an ingredient combination having quantities of nutrition that are not among nutrients of beneficial instruction set may be more distant, under distance metric, from beneficial instruction set than another ingredient combination having comparable quantities of target nutrients but lacking the non-target nutrients of the former combination; thus, an otherwise desirable meal having additional ingredients such as added sugar or fat may be more distant from a beneficial ingredient combination, and thus be less likely to be recommended. Selection of candidate ingredient lists may be performed at computing device 104; alternatively or additionally, computing device 104 may generate a client-side program that configures an alimentary provider device to perform any or all steps described above for selection of candidate ingredient lists. For instance, computing device 104 may transmit beneficial ingredient classifier to alimentary provider device and/or via client-side program, enabling selection to be performed using beneficial ingredient classifier and/or distance metric at alimentary provider device.

With continued reference to FIG. 1, computing device 104 may be configured to select at least a recommended ingredient combination 160 from the plurality of candidate ingredient combinations. Computing device 104 may perform selection by identifying one or more goal parameters and selecting utilizing the one or more goal parameters. As used in this disclosure, a "goal parameter" is a datum, other than a nutrient quantity, describing a candidate ingredient combination. A goal parameter may include, without limitation, a time of delivery of a candidate ingredient combination, an amount of time to prepare a candidate ingredient combination, an identity of a dish to be prepared using candidate ingredient combination, a cost of candidate ingredient combination such as a cost to be paid to a user, a cost of delivery, a delivery transit time, and/or a rating such as a quantitative rating of a preparer such as a chef, a quantitative rating of the dish, a quantitative rating of the alimentary provider, a quantitative rating of a delivery service, or the like. Qualitative ratings may include customer ratings collected using customer satisfaction surveys, expert ratings by reviewers, or the like.

Still referring to FIG. 1, at least a goal parameter may include at least a default parameter; for instance, as a default, computing device 104 may set as goal parameters a minimal cost, a delivery time below a certain threshold, and maximal qualitative ratings for one or more aspects of delivery. Alternatively or additionally, computing device 104 may receive at least a user parameter and select at least a recommended ingredient combination from the plurality of candidate ingredient combinations to match the at least a user parameter; user parameter may, for instance be added to and/or used to modify at least a default goal parameter. For instance, user may set as a goal parameter a particular dish the user is interested in consuming; user may select the dish, for instance and without limitation by being provided a list of dishes representing beneficial ingredient combinations, e.g. by being composed of ingredients of a beneficial ingredient combination, and selecting one displayed dish. User may set a particular price range, a particular delivery time and/or duration, or the like that interests the user. User may also provide inputs describing relative importance to user of each goal parameter, whether set by system 100 or user entered.

Further referring to FIG. 1, computing device 104 may receive provider parameters 156 from alimentary provider devices; parameter parameters may include values corresponding to any or all categories of goal parameters as described above. In an embodiment, provider parameters may be viewed as "bids" from alimentary providers seeking to have services and/or products utilized by user via system 100; bids and/or sets of provider parameters may be compared to any or all goal parameters to select an alimentary provider to provide user with a meal matching a candidate ingredient set. Some provider parameters may not be provided by an alimentary provider itself; for instance, provider parameters may include qualitative reviews from third party sites and/or devices. As a further example, delivery options, times, costs, or the likes may be provided directly by alimentary provider and/or by one or more devices operated by and/or used by one or more third-party delivery services.

With continued reference to FIG. 1, computing device 104 may perform machine-learning algorithms using a loss function analysis to select a recommended ingredient combination from plurality of candidate ingredient combinations. In an embodiment, computing device 104 may compare one or more user specific inputs to a mathematical expression representing a plurality of goal parameters. Mathematical expression may include a linear combination of variables, weighted by coefficients representing relative importance of each goal parameter. For instance, a variable such as food quality, importance to user of organic ingredients versus nonorganic ingredients may be multiplied by a first coefficient representing the importance of organic food standards, a second user input such as total cost may be multiplied by a second coefficient representing the importance of cost, a degree of variance from a and/or classified beneficial ingredient set may be represented as another parameter, which may be multiplied by another coefficient representing the importance of that parameter, a degree of variance from a preference for fresh or frozen ingredients may be multiplied by an additional coefficient representing an importance of that parameter, or the like; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, computing device 104 may calculate variables of set of provider parameters and/or variance of such parameters from goal parameters calculate an output of mathematical expression using the variables, and select candidate ingredient combination that produces an output having the lowest size, according to a given definition of "size," of the set of outputs representing each of plurality of candidate ingredient combinations; size may, for instance, included absolute value, numerical size, or the like. Selection of different loss functions may result in identification of different candidate ingredient combinations as generating minimal outputs; for instance, where organic ingredients is associated in a first loss function with a large coefficient or weight, a candidate ingredient combination having a small coefficient or weight for organic ingredients may minimize the first loss function, whereas a second loss function wherein organic ingredients has a smaller coefficient but degree of variance from cost goal which has a larger coefficient may produce a minimal output for a different candidate ingredient combination having a larger organic ingredients but more closely hewing to a cost goal.

Alternatively or additionally, and still referring to FIG. 1, each candidate ingredient combination may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each parameter. A candidate ingredient combination having a mathematical expression minimizing the error function may be selected, as representing an optimal expression of relative importance of parameters to a system or user. In an embodiment, error function and loss function calculations may be combined; for instance, a candidate ingredient combination resulting in a minimal aggregate expression of error function and loss function, such as a simple addition, arithmetic mean, or the like of the error function with the loss function, may be selected, corresponding to an option that minimizes total variance from goal parameters while simultaneously minimizing a degree of variance from a set of priorities corresponding to goal parameters. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each parameter to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function, such as without limitation using a regression algorithm. Mathematical expression and/or loss function may be user-specific, using a training set composed of past user selections; mathematical expression and/or loss function may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of candidate ingredient combinations. Use of regression to derive loss functions, loss function coefficients, and/or mathematical expressions may be performed, without limitation, as described in U.S. Nonprovisional application Ser. No. 16/502,835.

Still referring to FIG. 1, computing device 104 may alternatively or additionally filter candidate ingredient combinations according to one or more goal parameters and/or user entries. For instance, user may specify a desired meal, and computing device 104 may eliminate candidate ingredient combinations that do not match the user entry; as further non-limiting examples, candidate ingredient combinations that do not match user entries specifying a user maximal price, a maximal wait and/or transport time, or the like may be eliminated as well. Such filtration may be followed by presentation of filtered candidate ingredient combinations to user, and/or further selection of at least a recommended ingredient combination using additional processes such as loss function use as described above.

In an embodiment, computing device 104 may be configured to display at least a recommended ingredient combination to user. Computing device 104 may receive a user selection of a recommended ingredient combination, for instance by way of user selection of a link, button and/or other display element corresponding to a recommended ingredient combination. Computing device 104 may automatically initiate preparation and/or delivery of selected recommended ingredient combination, for instance and without limitation by transmitting indication of selection to a corresponding alimentary provider device.

In an embodiment, and still referring to FIG. 1, one or more candidate ingredient combinations and/or recommended ingredient combinations may be filtered out and/or eliminated prior to presentation to user if the one or more candidate ingredient combinations and/or recommended ingredient combinations are determined to violate a user-specific proscription. A "user-specific proscription," as used in this disclosure, is an element of data indicating that a user cannot receive an ingredient, nutrient, and/or combination of ingredients. A user-specific proscription may include, without limitation, a health-related reason the user receive and/or consume the ingredient, nutrient, and/or combination of ingredients, such as an allergy, sensitivity, or other medical condition such as without limitation phenylketonuria, a medical condition preventing participation in an activity and/or receipt of a pharmaceutical product, a moral, religious, and/or philosophical prohibition on receipt of thereof, or the like. User-specific proscriptions may include, as a non-limiting example, restrictions imposed by kosher and/or halal dietary rules User selection may be used as an addition to training data.

User selection may be used to deduct nutrients from alimentary instruction set 108.

Figure 3:
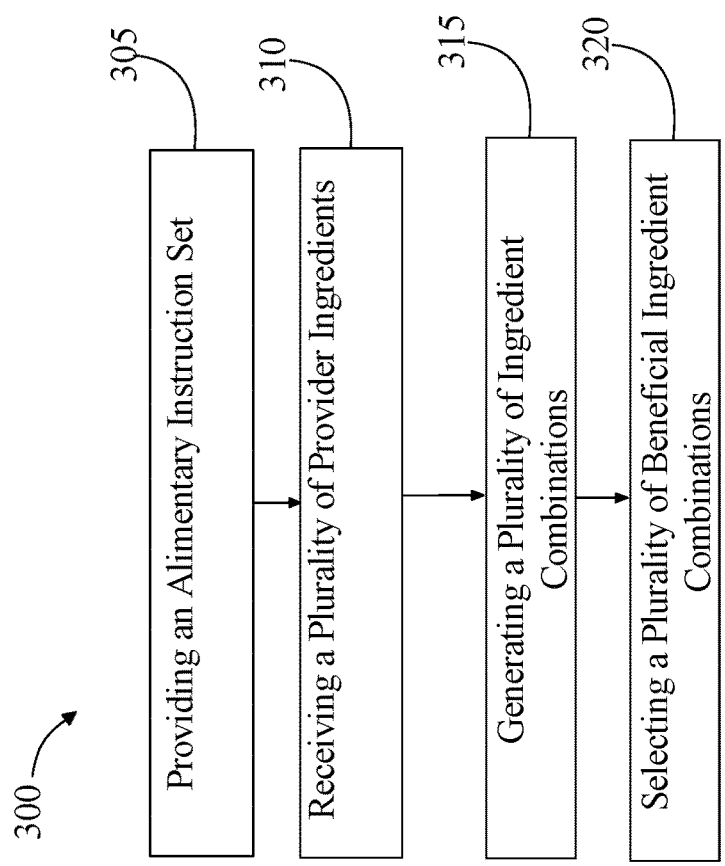
FIG. 3 is a flow diagram of an exemplary embodiment of a method for alimentary provisioning.

Referring now to FIG. 3, an exemplary embodiment of a method 300 of alimentary provisioning is illustrated. At step 305, a computing device 104 provide an alimentary instruction set 108 including a plurality of target nutrient quantities; this may be accomplished, without limitation, as described above in reference to FIG. 1. For instance, and without limitation, computing device 104 may provide alimentary instruction set 108 by receiving training data, recording at least a biological extraction from a user, training a machine-learning process using the training data, and, generating the at least an alimentary instruction set 108 as a function of biological extraction and using the machine-learning process, for instance as described above in reference to FIG. 1.

At step 310, and still referring to FIG. 3, computing device 104 receives, from each alimentary provider device of a plurality of alimentary provider devices, a plurality of provider ingredients; this may be accomplished, without limitation, as described above in reference to FIG. 1. For instance and without limitation, receiving the plurality of provider ingredients may include transmitting, to each alimentary provider device, a plurality of instruction ingredients and receiving, from each alimentary provider device, a plurality of matching ingredients. Computing device 104 may identify plurality of instruction ingredients as a function of the target nutrient quantities, for instance as described above. In an embodiment, and as described above in reference to FIG. 1, each of the two or more ingredients may be received from a single provider of the plurality of providers.

At step 315, and still referring to FIG. 3, computing device 104 generates a plurality of ingredient combinations, wherein each ingredient combination is a combination of two or more provider ingredients of the plurality of provider ingredients; this may be accomplished, without limitation, as described above in reference to FIG. 1.

At step 320, and continuing to refer to FIG. 3, computing device 104 selects a plurality of beneficial ingredient combinations from the plurality of ingredient combinations; this may be accomplished, without limitation, as described above in reference to FIG. 1. Computing device 104 may select at least an ingredient combination by determining a nutrient listing corresponding to each ingredient combination of the plurality of ingredient combinations, creating a distance metric from the nutrient listing to the alimentary instruction listing, and selecting at least an ingredient listing that minimizes the distance metric, selecting the plurality of beneficial ingredient combinations to minimize the distance metric, for instance as described above in reference to FIG. 1. Computing device 104 may select ingredient combination using a classifier, for instance as described above.

Still referring to FIG. 3, computing device 104 may select a plurality of candidate ingredient combinations, for instance as described above in reference to FIG. 1. For instance, and without limitation, selecting the plurality of candidate ingredient combinations may include receiving, from each provider device, a plurality of provider ingredient combinations and selecting a plurality of candidate ingredient combinations matching a beneficial ingredient combination of the plurality of beneficial ingredient combinations. As a further example, selecting the at least a provider ingredient combination may include generating a distance metric from each provider ingredient combination of the plurality of provider ingredient combinations to beneficial ingredient combinations of the plurality of beneficial ingredient combinations, and selecting the at least a provider ingredient combination that minimizes the distance metric, for instance as described above in reference to FIG. 1. Selecting at least a provider ingredient combination may include selecting the at least a provider ingredient combination using a classifier, for instance as described above in reference to FIG. 1.

With continued reference to FIG. 3, computing device 104 may receive at least a user parameter and select at least a beneficial ingredient combination from the plurality of candidate ingredient combinations to match the at least a user parameter, which may be implemented, without limitation, as described above in reference to FIG. 1.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
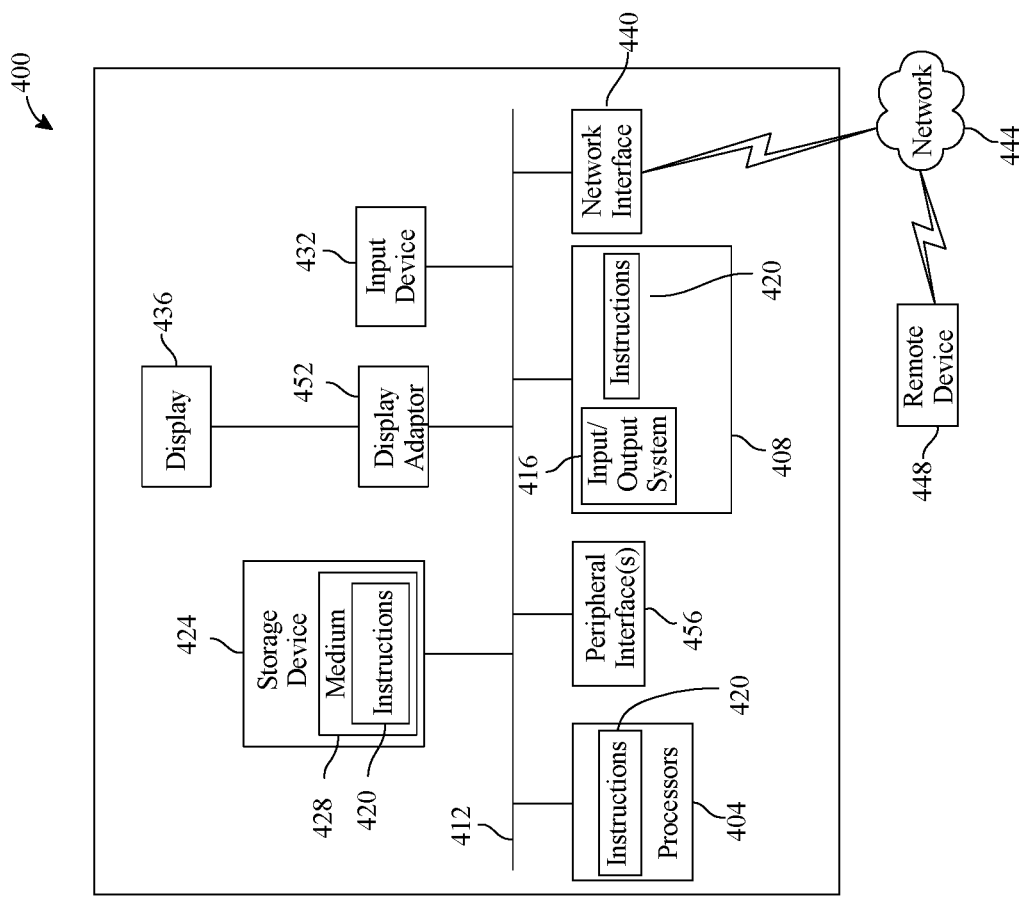
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIREWIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for alimentary provisioning, the system comprising a computing device configured to:
record at least a biological extraction from a user;
generate an alimentary instruction set for the user including a plurality of target nutrient quantities, wherein generating the alimentary instruction set comprises:
training a first machine-learning model using first training data, wherein the first training data is represented in vector form and includes biological extraction data correlated with target nutrition quantity data;
inputting the at least a biological extraction to the trained first machine-learning model; and
outputting the alimentary instruction set from the trained machine-learning model as a function of the at least a biological extraction;
receive, from each alimentary provider device of a plurality of alimentary provider devices, a plurality of provider ingredients;
generate a plurality of ingredient combinations, wherein each ingredient combination is a combination of two or more provider ingredients of the plurality of provider ingredients; and
select a plurality of beneficial ingredient combinations for the user from the plurality of ingredient combinations, wherein selecting the plurality of ingredient combinations further comprises:
determining a nutrient listing corresponding to each ingredient combination of the plurality of ingredient combinations;
creating a distance metric from each nutrient listing to the alimentary instruction set, wherein creating the distance metric comprises:
representing each nutrient listing as a first vector;
representing the target nutrient quantities as a second vector; and
determining a quantitative value indicating a similarity between the first vector and the second vector, wherein the quantitative value includes a cosine similarity between the first vector and the second vector;
selecting at least an ingredient listing that minimizes the distance metric based on the cosine similarity between the first vector and the second vector; and
selecting the plurality of beneficial ingredient combinations as a function of the at least an ingredient listing that minimizes the distance metric.

2. The system of claim 1, wherein the computing device is configured to receive the plurality of provider ingredients by:
transmitting, to each alimentary provider device, a plurality of instruction ingredients; and
receiving, from each alimentary provider device, a plurality of matching ingredients.

3. The system of claim 2, wherein the computing device is further configured to identify the plurality of instruction ingredients as a function of the target nutrient quantities.

4. The system of claim 1, wherein each of the two or more provider ingredients are received from a single alimentary provider device of the plurality of alimentary provider devices.

5. The system of claim 1, wherein the computing device is configured to select at least one beneficial ingredient combination using a classifier.

6. The system of claim 1, wherein the computing device is configured to select a plurality of candidate ingredient combinations, wherein selecting the plurality of candidate ingredient combinations further comprises:
receiving, from each alimentary provider device, a plurality of provider ingredient combinations; and
selecting the plurality of candidate ingredient combinations matching a beneficial ingredient combination of the plurality of beneficial ingredient combinations.

7. The system of claim 6, wherein selecting at least a provider ingredient combination further comprises:
generating a distance metric from each provider ingredient combination of the plurality of provider ingredient combinations to beneficial ingredient combinations of the plurality of beneficial ingredient combinations; and
selecting the at least a provider ingredient combination that minimizes the distance metric.

8. The system of claim 7, wherein the computing device is configured to select the at least a provider ingredient combination using a classifier.

9. The system of claim 6 wherein the computing device is configured to:
receive at least a user parameter; and
select at least a recommended ingredient combination from the plurality of candidate ingredient combinations to match the at least a user parameter.

10. A method of alimentary provisioning, the method comprising:
recording at least a biological extraction from a user;
generating an alimentary instruction set for the user including a plurality of target nutrient quantities, wherein generating the alimentary instruction set comprises:
training a first machine-learning model using first training data, wherein the first training data is represented in vector form and includes biological extraction data correlated with target nutrition quantity data;
inputting the at least a biological extraction to the trained first machine-learning model; and
outputting the alimentary instruction set from the trained machine-learning model as a function of the at least a biological extraction;
receiving, from each alimentary provider device of a plurality of alimentary provider devices, a plurality of provider ingredients;
generate a plurality of ingredient combinations, wherein each ingredient combination is a combination of two or more provider ingredients of the plurality of provider ingredients;
selecting a plurality of beneficial ingredient combinations for the user from the plurality of ingredient combinations, wherein selecting the plurality of ingredient combinations further comprises:
determining a nutrient listing corresponding to each ingredient combination of the plurality of ingredient combinations;
creating a distance metric from each nutrient listing to the alimentary instruction set, wherein creating the distance metric comprises:
representing each nutrient listing as a first vector;
representing the target nutrient quantities as a second vector; and
determining a quantitative value indicating a similarity between the first vector and the second vector, wherein the quantitative value includes a cosine similarity between the first vector and the second vector;

selecting at least an ingredient listing that minimizes the distance metric based on the cosine similarity between the first vector and the second vector; and selecting the plurality of beneficial ingredient combinations as a function of the at least an ingredient listing that minimizes the distance metric.

11. The method of claim 10, wherein receiving the plurality of provider ingredients further comprises:

transmitting, to each alimentary provider device, a plurality of instruction ingredients; and receiving, from each alimentary provider device, a plurality of matching ingredients.

12. The method of claim 11 further comprising identifying the plurality of instruction ingredients as a function of the target nutrient quantities.

13. The method of claim 10, wherein each of the two or more provider ingredients are received from a single alimentary provider device of the plurality of alimentary provider devices.

14. The method of claim 10 further comprising selecting at least one beneficial ingredient combination using a classifier.

15. The method of claim 10 further comprising selecting a plurality of candidate ingredient combinations, wherein selecting the plurality of candidate ingredient combinations further comprises:

receiving, from each alimentary provider device, a plurality of provider ingredient combinations; and selecting the plurality of candidate ingredient combinations matching a beneficial ingredient combination of the plurality of beneficial ingredient combinations.

16. The method of claim 15, wherein selecting at least a provider ingredient combination further comprises:

generating a distance metric from each provider ingredient combination of the plurality of provider ingredient combinations to beneficial ingredient combinations of the plurality of beneficial ingredient combinations; and selecting the at least a provider ingredient combination that minimizes the distance metric.

17. The method of claim 16 further comprising selecting the at least a provider ingredient combination using a classifier.

18. The method of claim 15 further comprising:

receiving at least a user parameter; and selecting at least a recommended ingredient combination from the plurality of candidate ingredient combinations to match the at least a user parameter.

* * * * *